United States Patent
Tipler et al.

(10) Patent No.: US 7,691,181 B2
(45) Date of Patent: *Apr. 6, 2010

(54) SYSTEM FOR CONTROLLING FLOW INTO CHROMATOGRAPHIC COLUMN USING TRANSFER LINE IMPEDANCE

(75) Inventors: Andrew Tipler, Trumbull, CT (US); Richard G Edwards, Brookfield, CT (US)

(73) Assignee: PerkinElmer LAS, Inc., Boston, MA (US)

( * ) Notice: Subject to any disclaimer, the term of this patent is extended or adjusted under 35 U.S.C. 154(b) by 11 days.

This patent is subject to a terminal disclaimer.

(21) Appl. No.: 12/332,539

(22) Filed: Dec. 11, 2008

(65) Prior Publication Data

US 2009/0084261 A1    Apr. 2, 2009

Related U.S. Application Data

(63) Continuation of application No. 11/432,158, filed on May 11, 2006, now Pat. No. 7,468,095.

(60) Provisional application No. 60/680,334, filed on May 12, 2005, provisional application No. 60/681,747, filed on May 17, 2005.

(51) Int. Cl.
  *B01D 53/02* (2006.01)
(52) U.S. Cl. ............... 95/82; 95/87; 96/102; 96/105; 96/106; 73/23.41; 73/23.42
(58) Field of Classification Search .......... 95/82, 95/85, 87, 89; 73/23.35, 23.36, 23.41, 23.42; 422/89; 96/101, 102, 103, 105, 106
See application file for complete search history.

(56) References Cited

U.S. PATENT DOCUMENTS 3,405,551 A    10/1968  Halasz (Continued)

FOREIGN PATENT DOCUMENTS

DE    4316375 C1    6/1994

(Continued)

OTHER PUBLICATIONS

Chenghong Li et al. Optimal Packing Characteristics of Rolled, Continuous Stationary-Phase Columns American Chemical Society and American Institute of Chemical Engineers Published on web Feb. 13, 2002, pp. 309-316.

(Continued)

*Primary Examiner*—Michael A Marcheschi
*Assistant Examiner*—Robert A Clemente
(74) *Attorney, Agent, or Firm*—St. Onge Steward Johnston & Reens LLC

(57) ABSTRACT

A system for controlling the flow rate into a chromatographic column is disclosed generally comprising communicating a fluid to the column through a transfer line, measuring the inlet pressure, determining the outlet pressure, and adjusting the applied pressure until the inlet and outlet pressures produce a desired flow rate for the transfer line outlet. In certain embodiments, the applied pressure is adjusted by controlling a proportional valve. In some embodiments, the outlet pressure is determined by measuring the pressure drop across the transfer line and calculating the outlet pressure from the measured inlet pressure and the pressure drop.

29 Claims, 3 Drawing Sheets

U.S. PATENT DOCUMENTS

| | | | |
|---|---|---|---|
| 4,962,662 A | 10/1990 | Berger | |
| 5,545,252 A | 8/1996 | Hinshaw et al. | |
| 5,711,786 A | 1/1998 | Hinshaw | |
| 5,952,556 A | 9/1999 | Shoji | |
| 6,338,823 B1 | 1/2002 | Furukawa | |
| 6,341,520 B1 | 1/2002 | Satoh et al. | |
| 6,494,078 B1 | 12/2002 | Klee | |
| 6,652,625 B1 | 11/2003 | Tipler et al. | |
| 6,813,929 B2 | 11/2004 | Jochum, Jr. | |
| 7,111,494 B2 * | 9/2006 | Tipler | 73/23.36 |
| 7,135,056 B2 | 11/2006 | Henderson | |
| 7,168,296 B2 * | 1/2007 | Tipler et al. | 73/37 |
| 7,422,625 B2 * | 9/2008 | Tipler et al. | 95/82 |
| 7,437,906 B2 * | 10/2008 | Boursier Niutta et al. | 73/23.27 |
| 7,468,095 B2 * | 12/2008 | Tipler et al. | 95/82 |
| 2002/0194898 A1 | 12/2002 | Klee | |
| 2005/0155409 A1 | 7/2005 | Niutta et al. | |
| 2005/0210957 A1 | 9/2005 | Tipler et al. | |
| 2005/0284209 A1 | 12/2005 | Tipler et al. | |
| 2006/0016245 A1 | 1/2006 | Tipler et al. | |

FOREIGN PATENT DOCUMENTS

| | | | |
|---|---|---|---|
| EP | 0730151 | A2 | 9/1996 |
| GB | 2310611 | A | 9/1997 |
| WO | 0225391 | A1 | 3/2002 |
| WO | 03071265 | A1 | 8/2003 |
| WO | 2004013578 | A2 | 2/2004 |
| WO | 2004053478 | A1 | 6/2004 |
| WO | 2005088296 | A1 | 9/2005 |

OTHER PUBLICATIONS

F.R. Gonzalez et al. "Theoretical and practical aspects of flow control in programmed-temperature gas chromatography" Journal Of Chromatography, Elsevier Science Publishers B.V. Amsterdam, NL, vol. 757, No. 1-2, Jan. 3, 1997, pp. 97-107.

International Search Report, PCT/US2006/018890, Oct. 5, 2006, 4 pages.

L.M. Blumberg. "Method Translation and Retention Time Locking in Partition GC" Analytical Chemistry, American Chemical Society. Columbus, US, vol. 70 No. 18, Sep. 15, 1998, pp. 3828-3839.

R. Shellie, P. Marriott, P. Morrison, L. Mondello. "Effects of pressure drop on absolute retention matching in comprehensive two-dimensional gas chromatography" Journal Of Separation Science, vol. 27, No. 7-8, May 7, 2004, pp. 504-512.

* cited by examiner

SYSTEM FOR CONTROLLING FLOW INTO CHROMATOGRAPHIC COLUMN USING TRANSFER LINE IMPEDANCE

CROSS-REFERENCE TO RELATED APPLICATIONS

This patent application is a continuation of U.S. patent application Ser. No. 11/432,158, filed May 11, 2006, now U.S. Pat. No. 7,468,095, which claims the benefit of, under Title 35, United States Code, Section 119(e), U.S. Provisional Patent Application Ser. No. 60/680,334, filed May 12, 2005, and U.S. Provisional Patent Application Ser. No. 60/681,747, filed May 17, 2005, the contents of each of which are herein incorporated by reference in their entirety.

FIELD OF THE INVENTION

The present invention relates to a systems and methods for controlling the flow rate of fluid into a chromatographic column. More specifically, the invention relates to systems and methods that include controlling the flow rate of the fluid based on the impedance of a transfer line used to communicate the fluid to the column.

BACKGROUND OF THE INVENTION

Gas chromatography is essentially a physical method of separation in which constituents of a vapor sample in a carrier gas are adsorbed or absorbed and then desorbed by a stationary phase material in a column. A pulse of the sample is introduced into a steady flow of carrier gas, which carries the sample into a chromatographic column. The inside of the column is lined with a liquid, and interactions between this liquid and the various components of the sample—which differ based upon differences among partition coefficients of the elements—cause the sample to be separated into the respective elements. At the end of the column, the individual components are more or less separated in time. Detection of the gas provides a time-scaled pattern, typically called a chromatogram, that, by calibration or comparison with known samples, indicates the constituents, and the specific concentrations thereof, which are present in the test sample. An example of the process by which this occurs is described in U.S. Pat. No. 5,545,252 to Hinshaw.

In some applications, a fluid source, such as a carrier gas supply and/or a sampling device, such as a headspace sampler or thermal desorption unit, is connected to the chromatographic column via a transfer line. This transfer line, which may, for example, comprise a length of fused silica tubing, communicates the fluid from the source to the column for separation and detection. In certain applications, an additional device may also be provided for performing some additional pre-concentration of analytes, such as in the system disclosed in U.S. Pat. No. 6,652,625 to Tipler, the contents of which are herein incorporated by reference in their entirety.

In some applications, as the column is heated, the viscosity of the gas flowing through it likewise increases. As a result, under isobaric conditions—where the carrier gas is applied at a constant pressure—the flow rate through the column will decrease as the temperature of the column increases. Though this usually has no detrimental effect on system performance in some applications, in other applications, such as those that employ a flow-sensitive detector, such as a mass spectrometer, the effect on performance can be dramatic.

The viscosity varies with respect to changes in temperature in a relatively predictable manner for the common carrier gases—a relationship that can be approximated according to the equation:

$$\eta_c = \eta_0 \left(\frac{T_c}{T_0}\right)^x \quad (1)$$

where:
  $\eta_c$ is the viscosity at column temperature $T_c$
  $\eta_0$ is the viscosity at absolute temperature $T_0$ (from published tables)
  x is a dimensionless constant The coefficients for the three most common carrier gases, for example, are provided in the following table:

TABLE 1

| Gas | $T_0$ (K) | $\eta_0$ (Pa · s × $10^{-6}$) | x |
|---|---|---|---|
| Hydrogen | 273.2 | 8.399 | 0.680 |
| Nitrogen | 273.2 | 16.736 | 0.725 |
| Helium | 273.2 | 18.662 | 0.646 |

Accordingly, by determining the column temperature $T_c$, one can determine the viscosity $\eta_c$ using Equation 1 and Table 1.

When the viscosity $\eta_c$ is determined, presuming the column dimensions are known, a specific flow rate can be entered and maintained using the Hagen-Poiseuille equation as follows:

$$F_o = \frac{\pi \cdot d_c^4 \cdot (P_i^2 - P_o^2)}{256 \cdot L_c \cdot \eta_c \cdot P_o} \quad (2)$$

Where:
  $F_o$ is the flow rate at the column outlet
  $d_c$ is the internal diameter of the column
  $L_c$ is the length of the column
  $\eta_c$ is the viscosity of the carrier gas in the column
  $P_i$ is the carrier gas pressure at the column inlet
  $P_o$ is the carrier gas pressure at the column outlet Some gas chromatographs are equipped with electronic programmable pneumatic controls. Therefore, because the relationship between viscosity and temperature is well known as described above, and because the GC oven temperature is known due to the fact that it is controlled by the same system, the chromatograph is able to readily compensate for the above-described changes in gas viscosity by increasing the column inlet pressure at a rate calculated to maintain a constant (isochoric) flow rate through the column.

In some applications, however, the gas pressure is controlled on a device remote from the chromatograph, such as a sampling device. This requires that the sampling device have constant knowledge of the column temperature in order to calculate the viscosity at that temperate and make the appropriate adjustments to the applied pressure.

Accordingly, another solution that has been proposed is to monitor the temperature of the column, as is disclosed in U.S. Patent Application No. 2006/0016245 by Tipler et al, the contents of which are herein incorporated by reference in their entirety. In such systems, a temperature sensor may be employed to measure the temperature of the column and communicate this measurement to the sampling device, and the sampling device then adjusts the pressure at which it supplies the fluid based, in part, upon this temperature.

In order to effect the above-described pressure compensatory approach, the sampling device must know the geometry and temperature of both the transfer line and the column, unless the pressure is controlled at an interface between the two. In some cases, an interface device is employed to control the flow rate of the fluid flowing into the chromatographic column. For example, in U.S. Patent Application No. 2005/0284209 by Tipler et al, the contents of which are herein incorporated by reference in their entirety, a system is disclosed in which a chromatographic injector interfaces a transfer line with the column, and this injector is used to control the flow rate at the column inlet.

SUMMARY OF THE INVENTION

The present teachings include systems and methods for controlling the flow rate of a fluid into a chromatographic column such that a substantially constant flow rate through the column is maintained as the column temperature changes. Further, systems and methods are provided for controlling the flow rate of a fluid into a chromatographic column that does not require knowledge of the geometry and temperature of both the transfer line and the column. Additionally, systems and methods are provided for controlling the flow rate of a fluid into a chromatographic column that does not require an additional interface device. Also, systems and methods are provided that minimize user input and human error.

To achieve at least some of the objects listed, the invention comprises a method for controlling the flow into a chromatographic column, including communicating a fluid through a transfer line to a chromatographic column, determining the inlet pressure at an inlet end of the transfer line, determining the outlet pressure at an outlet end of the transfer line, and adjusting the pressure at the inlet end of the transfer line to produce a desired flow rate at the outlet end of the transfer line based on the determined inlet and outlet pressures.

In another embodiment, the invention comprises a method for controlling the flow into a chromatographic column, including receiving the gas supplied by the sampling device, providing a transfer line through which the gas is communicated from the sampling device to the column and through which the gas flows from a inlet end to an outlet end, selecting a desired flow rate for the fluid flowing out of the transfer line and into the column, determining the pressure at the inlet end of the transfer line, determining the pressure at the outlet end of the transfer line, and adjusting the pressure at the inlet end of the transfer line until the determined inlet and outlet pressures produce the desired flow rate for the fluid flowing into the column.

In some of these embodiments, the inlet pressure is adjusted by adjusting a proportional valve.

In certain embodiments, the inlet pressure is determined by measuring the pressure at the inlet end of the transfer line with a pressure transducer. In some of these embodiments, the outlet pressure is determined by measuring the pressure drop across the transfer line with a differential pressure transducer, and then calculating the outlet pressure from the measured inlet pressure and the measured pressure drop. In other embodiments the outlet pressure is determined by measuring the pressure at the outlet end of the transfer line with a pressure transducer.

In some embodiments, the invention further includes calculating an expected pressure drop across the column at the desired flow rate, measuring the actual pressure drop across the column, and comparing the expected pressure drop to the actual pressure drop.

In yet another embodiment, the invention comprises a system for controlling the flow into a chromatographic column, including a transfer line that communicates a fluid to a chromatographic column, the transfer line having an inlet end and an outlet end, a valve that controls the pressure of the fluid at the inlet end of the transfer line, a first pressure transducer that measures the pressure at the inlet end of the transfer line, a second pressure transducer for determining the pressure at the outlet end of the transfer line, and a controller that receives signals from the first and second transducers and, in response thereto, adjusts the valve to establish a desired flow rate at the outlet end of the transfer line.

In certain embodiments, the invention includes a heating assembly in which the transfer line is disposed for controlling the temperature of the transfer line.

In some of these embodiments, the sampling device is a headspace sampler, while in other embodiments, the sampling device is a headspace sampler.

DETAILED DESCRIPTION OF THE INVENTION

Figure 1:
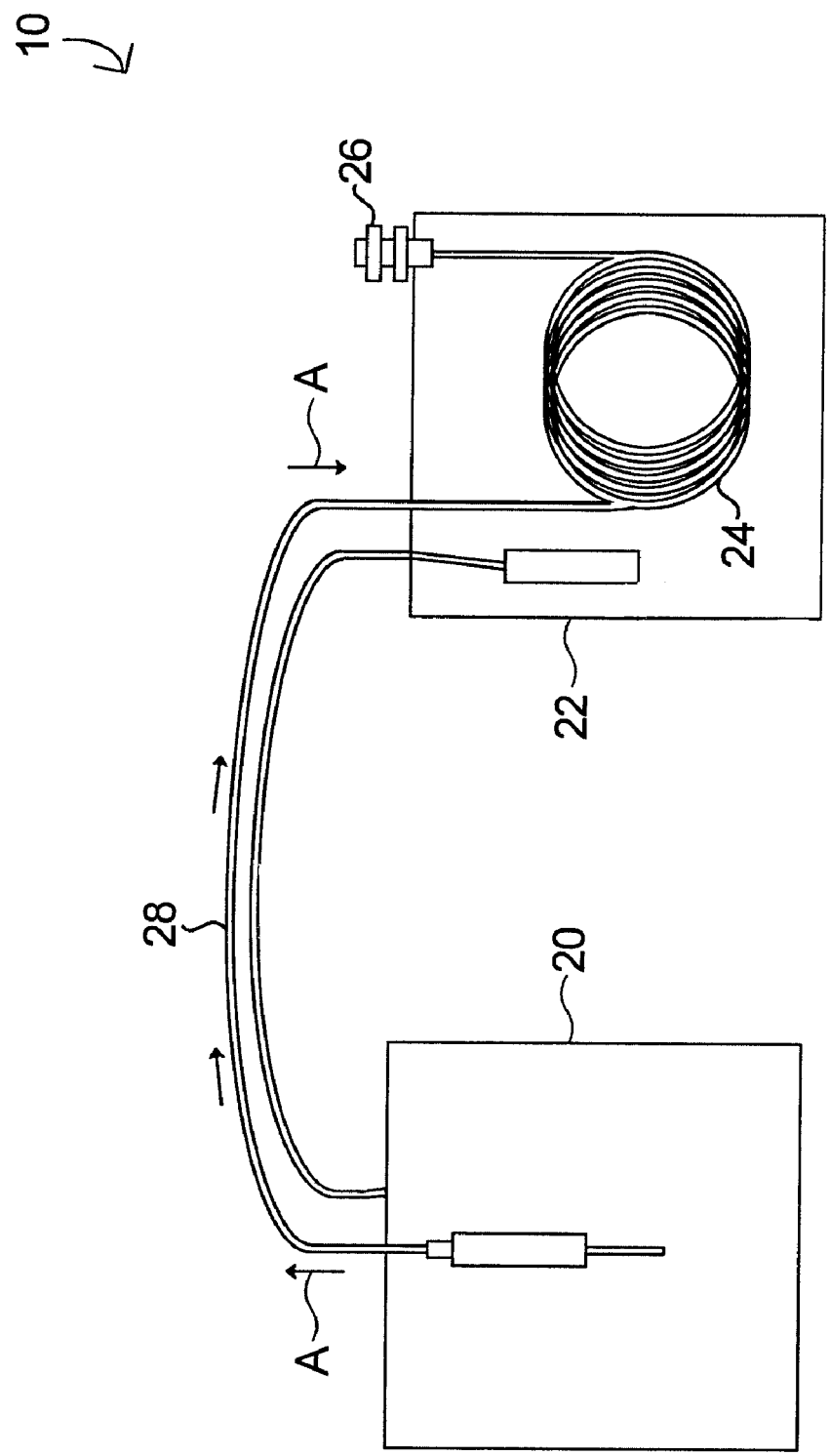
FIG. 1 is schematic view of sampling system in accordance with the invention.
Figure 2:
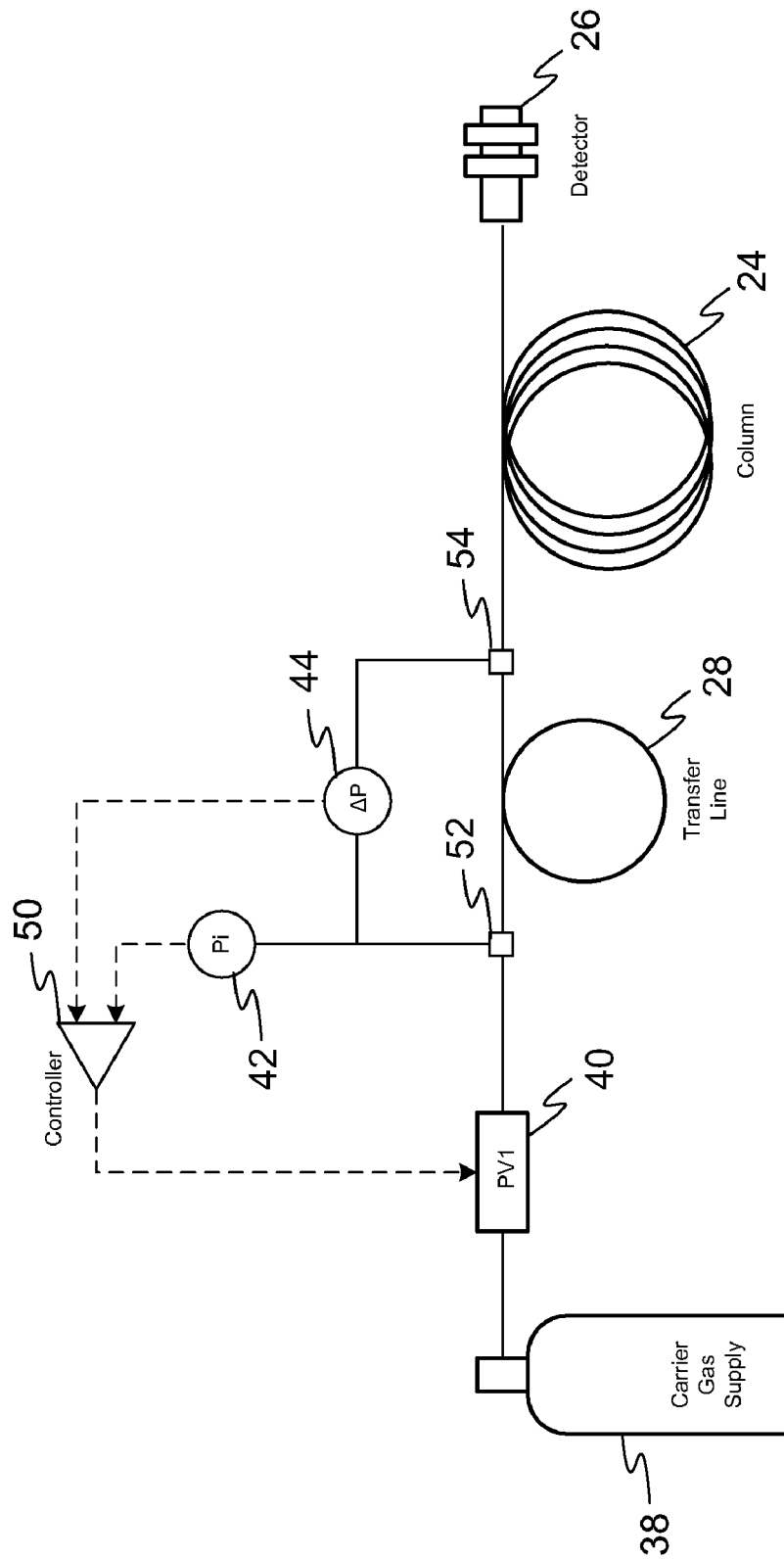
FIG. 2 is a schematic view of the use of pressure drop measurements to control the flow rate in the system of FIG. 1.

The basic components of one embodiment of a system for controlling flow rate into a chromatographic column in accordance with the invention are illustrated in FIGS. 1-2. As used in the description, the terms "top," "bottom," "above," "below," "over," "under," "above," "beneath," "on top," "underneath," "up," "down," "upper," "lower," "front," "rear," "back," "forward" and "backward" refer to the objects referenced when in the orientation illustrated in the drawings, which orientation is not necessary for achieving the objects of the invention.

The system 10 includes a source of fluid, such as sampling device 20, which, in the particular embodiment described below, is a thermal desorption unit, but, in other embodiments, may include other sampling devices, such as a headspace sampler. The system 10 further includes a gas chromatograph 22, which includes a chromatographic column 24 connected to a detector 26. The thermal desorption unit 20 is in fluid communication with the chromatograph 22 via a transfer line 28, through which a sample mixture is communicated from the unit 20 to the column 22 (indicated by arrows A).

The transfer line 28 comprises a length of tubing made from an inert material, such as, for example, deactivated fused silica or silica-coated stainless steel tubing. In some embodiments, the transfer line 28 is between about one and two meters long and has an internal diameter of less than 0.5 mm. Such tubing can be made with a reasonable tolerance, and thus, the internal geometry of the transfer line 28 is predictable.

Some chromatographic analyses monitor analyte concentrations at very low levels, which precludes the use of splits in the sample stream, and thus, the flow rate through the transfer line 28 is often the same as the flow rate through the column 24. In the case of capillary columns, this will sometimes mean a flow rate of less than 1 mL/min. In order to minimize longitudinal diffusion of the sample along the transfer line 28 at such low flow rates, it can be useful to keep the internal diameter of the transfer line 28 to a minimum in order to increase the velocity of the fluid, thereby minimizing the amount of time that the analytes reside in the transfer line 28. As the internal diameter is reduced, the flow impedance of the transfer line increases. Accordingly, in some embodiments, the transfer line 28 has an internal diameter between about 0.2 mm and 0.3 mm to produce a practically measurable pressure drop.

By assessing this pressure drop across the transfer line 28, the pressure at which the fluid must be applied in order to achieve a desired flow rate at the transfer line outlet (i.e., the column inlet) can be determined by using the Hagen-Poiseuille equation (Equation 2) for the transfer line (as opposed to the column), which can be simplified to:

$$F_o = \frac{a \cdot (P_i^2 - P_o^2)}{\eta \cdot P_o} \quad (3)$$

where a is a geometric constant, equal to $$\frac{\pi \cdot d_t^4}{256 \cdot L_t},$$

and where the viscosity η is determined using the temperature of the transfer line in accordance with Equation 1.

The transfer line 28 is normally surrounded by a concentric heating assembly 30, which prevents possible condensation of the sample material flowing through it. Though illustrated along only part of the transfer line 28 in FIG. 1, the heating assembly 30 typically extends along the length of the transfer line 28 in order to keep it hot along its entire length. In some embodiments, the heating assembly may comprises an inner, slightly rigid, stainless steel tube, approximately an eighth of an inch in diameter, through which the transfer line 28 is threaded, an a resistive heating coil wound around this tube. Insulators may then be provided around this coil, such as, for example, a fiber glass webbing, which may, in turn, be surrounded by a insulative foam. The temperature of the heater is normally thermostatted, and thus, the transfer line 28 is maintained at a constant temperature.

The aforementioned pressure drop assessment is illustrated in FIG. 2. A fluid source, such as the carrier gas supply 38 illustrated in FIG. 2, supplies fluid through a proportional valve 40. A first pressure transducer 42 measures the pressure at the transfer line inlet 52, and communicates this pressure $P_i$ to a controller 50. A differential pressure transducer 44 measures the change in pressure from the transfer line inlet 52 to its outlet 54, and likewise, communicates this value ΔP to the controller 50. Accordingly, the pressure at the transfer line outlet can be computed using the Equation:

$$P_o = (P_i - \Delta P) \quad (4)$$

Figure 3:
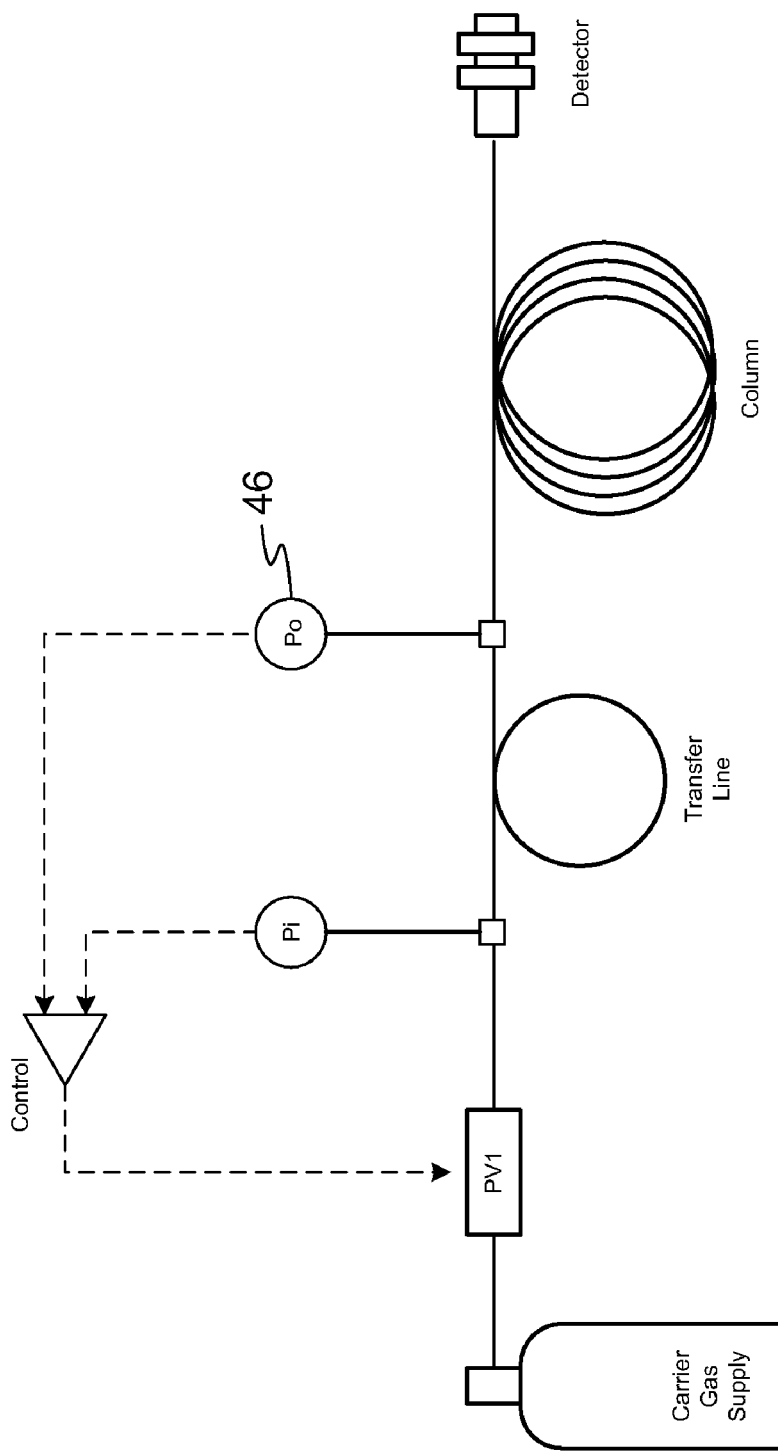
FIG. 3 is a schematic view of the use of outlet pressure measurements to control the flow rate in the system of FIG. 1.

In certain embodiments, as illustrated in FIG. 3, a second absolute transducer 46 can be employed to directly measure the outlet pressure $P_o$ instead of using the differential pressure transducer described above. However, due to the relative magnitudes of large pressures and small pressure drops, it can be useful to employ the differential transducer 44 shown in FIG. 2.

Using the measured values of $P_i$ and $P_o$, the controller 50 adjusts the proportional valve 40 until the measured/calculated inlet and outlet pressures, when entered into Equation 3, produce the desired flow rate $F_o$ for the transfer line outlet (column inlet). If the temperature changes, so will the viscosity, and thus, the flow rate, and therefore, adjustments must be made to the applied pressure to compensate for such changes.

During operation, the inlet pressure $P_i$ is adjusted directly by the proportional valve 40, while the pressure drop ΔP, while measurable, is not directly controlled. For this reason, the main electronic/firmware control loop (i.e., inner loop) will regulate $P_i$ at a fast rate to maintain system stability. Meanwhile, the outlet pressure (or the difference in pressure, from which the output pressure is calculated) will likewise be communicated to the same controller 50, but at a slower speed (i.e., outer loop). The proportional valve 40 will be adjusted until the combination of $P_i$ and ΔP produces the correct flow rate $F_o$ according to Equation 3.

As is evident, the efficacy of the calculations resulting from the use of Equation 3 will depend heavily on how accurately the geometry and temperature of the transfer line is defined. In practice, the internal diameter and exact temperature of the transfer line can be difficult to measure, and thus, in some cases, a system calibration may be performed. Accordingly, Equation 3 is slightly modified as follows:

$$F_o = \frac{a \cdot (P_i^2 - P_o^2)}{\eta_{(Ts+b)} \cdot P_o} \quad (5)$$

where:
$\eta_{(Ts+b)}$ is the viscosity of the carrier gas at set temperature $T_s$
b is the difference between the set temperature $T_s$ and the actual temperature of the transfer line The values of the constants a and b are then calculated by measuring the actual flow rate through the transfer line at two different temperature settings, plugging the measured rates into Equation 5, and solving the resultant simultaneous equations.

It is also important to note that the values for $F_o$ will be for the volumetric flow rate at the temperature and pressure at the outlet of the transfer line. Because this will normally be at an elevated temperature and possibly at a pressure different from ambient, the values for $F_o$ must be corrected to the flow rate measurements expected by the user, as it is normal practice to express (and apply) the flow rate corrected to Standard Ambient Temperature and Pressure (SATP), as shown below:

$$F_a = F_o \frac{P_o}{P_a} \cdot \frac{T_o}{T_a} \quad (6)$$

Where:
$F_a$ is the flow rate corrected to SATP
$P_a$ is the standard ambient absolute pressure (100 kPa)
$T_a$ is the standard ambient absolute temperature (298.15 K)
$T_o$ is the temperature at the transfer line outlet ($T_s$+b)

Though the above-described system permits an operator to control flow rate into a column without knowledge of the temperature or geometry of the column itself, in the event that these column parameters are known, the above described system can be further utilized to test for possible leaks and/or blockages. Using the Hagen-Poiseuille equation as applied to the column (Equation 2), the pressure drop across the column 24 can be predicted for a given flow rate. This predicted pressure drop can be compared to an actual pressure drop across the column 24 as the flow rate is being controlled as described above. If a significant difference is detected between the predicted and actual pressure drops, this would indicate the possible presence of a leak at the connection between the transfer line 28 and column 24 or a blockage in the transfer line or column.

It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

What is claimed is:

1. A method of controlling the flow into a chromatographic column, the method comprising:
   communicating a fluid through a transfer line to a chromatographic column;
   using a first pressure transducer to determine the inlet pressure at an inlet end of the transfer line;
   using a second pressure transducer to determine the outlet pressure at an outlet end of the transfer line; and
   controlling a proportional valve upstream of the first pressure transducer to adjust the pressure at the inlet end of the transfer line to produce a desired flow rate at the outlet end of the transfer line based on the determined inlet and outlet pressures.

2. The method of claim 1, wherein the step of using a second pressure transducer to determine the outlet pressure at an outlet end of the transfer line comprises:
   measuring the pressure drop across the transfer line with a differential pressure transducer; and
   calculating the outlet pressure from the measured inlet pressure and the measured pressure drop.

3. The method of claim 2, further comprising the steps of:
   calculating an expected pressure drop across the column at the desired flow rate;
   measuring the actual pressure drop across the column; and
   comparing the expected pressure drop to the actual pressure drop.

4. The method of claim 1, wherein the fluid communicated through the transfer line is sample gas supplied by a headspace sampler.

5. The method of claim 1, wherein the fluid communicated through the transfer line is sample gas supplied by a thermal desorption unit.

6. A system for controlling the flow into a chromatographic column, comprising:
   a sampling device that obtains a sample gas containing analytes to be measured, wherein said sampling device comprises a thermal desorption unit;
   a transfer line that communicates the sample gas from the sampling device to a chromatographic column, said transfer line having an inlet end and an outlet end;
   a valve that controls the pressure at the inlet end of said transfer line;
   a first pressure transducer that measures the pressure at the inlet end of said transfer line;
   a second pressure transducer for determining the pressure at the outlet end of the transfer line; and
   a controller that receives signals from said first and second transducers and, in response thereto, adjusts said valve to establish a desired flow rate at the outlet end of said transfer line.

7. The system of claim 6, wherein said second pressure transducer is a differential pressure transducer that measures the pressure drop across the transfer line, and wherein said controller calculates the pressure at the outlet end of said transfer line from the measured pressure at the inlet end and the measured pressure drop.

8. The system of claim 1, wherein said second pressure transducer is a pressure transducer that measures the pressure at the outlet end of said transfer line.

9. The system of claim 1, wherein said valve is a proportional valve.

10. The system of claim 1, further comprising a heating assembly in which said transfer line is disposed for controlling the temperature of said transfer line.

11. A system for controlling the flow into a chromatographic column, comprising:
    a transfer line that communicates a fluid to a chromatographic column, said transfer line having an inlet end and an outlet end;
    a heating assembly in which said transfer line is disposed for controlling the temperature of said transfer line;
    a first pressure transducer that measures the pressure at the inlet end of said transfer line;
    a second pressure transducer for determining the pressure at the outlet end of the transfer line;
    a valve positioned upstream of the first pressure transducer that controls the pressure of the fluid at the inlet end of said transfer line; and
    a controller that receives signals from said first and second transducers and, in response thereto, adjusts said valve to establish a desired flow rate at the outlet end of said transfer line.

12. The system of claim 11, wherein said second pressure transducer is a differential pressure transducer that measures the pressure drop across the transfer line, and wherein said controller calculates the pressure at the outlet end of said transfer line from the measured pressure at the inlet end and the measured pressure drop.

13. The system of claim 11, wherein said second pressure transducer is a pressure transducer that measures the pressure at the outlet end of said transfer line.

14. The system of claim 11, further comprising a fluid source from which said transfer line communicates the fluid to the column.

15. The system of claim 14, wherein said fluid source comprises a sampling device.

16. The system of claim 15, wherein said sampling device comprises a thermal desorption unit.

17. The system of claim 15, wherein said sampling device comprises a headspace sampler.

18. A system for controlling the flow into a chromatographic column, comprising:
    a sampling device that obtains a sample gas containing analytes to be measured, wherein said sampling device comprises a headspace sampler;
    a transfer line that communicates the sample gas from the sampling device to a chromatographic column, said transfer line having an inlet end and an outlet end;
    a valve that controls the pressure at the inlet end of said transfer line;
    a first pressure transducer that measures the pressure at the inlet end of said transfer line;
    a second pressure transducer for determining the pressure at the outlet end of the transfer line; and a controller that receives signals from said first and second transducers and, in response thereto, adjusts said valve to establish a desired flow rate at the outlet end of said transfer line.

19. The system of claim 18, wherein said second pressure transducer is a differential pressure transducer that measures the pressure drop across the transfer line, and wherein said controller calculates the pressure at the outlet end of said transfer line from the measured pressure at the inlet end and the measured pressure drop.

20. The system of claim 18, wherein said second pressure transducer is a pressure transducer that measures the pressure at the outlet end of said transfer line.

21. The system of claim 18, wherein said valve is a proportional valve.

22. The system of claim 18, further comprising a heating assembly in which said transfer line is disposed for controlling the temperature of said transfer line.

23. A system for controlling the flow into a chromatographic column, comprising:
- a sampling device that obtains a sample gas containing analytes to be measured;
- a transfer line that communicates the sample gas from the sampling device to a chromatographic column, said transfer line having an inlet end and an outlet end;
- a heating assembly in which said transfer line is disposed for controlling the temperature of said transfer line;
- a valve that controls the pressure at the inlet end of said transfer line;
- a first pressure transducer that measures the pressure at the inlet end of said transfer line;
- a second pressure transducer for determining the pressure at the outlet end of the transfer line; and
- a controller that receives signals from said first and second transducers and, in response thereto, adjusts said valve to establish a desired flow rate at the outlet end of said transfer line.

24. The system of claim 23, wherein said second pressure transducer is a differential pressure transducer that measures the pressure drop across the transfer line, and wherein said controller calculates the pressure at the outlet end of said transfer line from the measured pressure at the inlet end and the measured pressure drop.

25. The system of claim 23, wherein said second pressure transducer is a pressure transducer that measures the pressure at the outlet end of said transfer line.

26. The system of claim 23, wherein said valve is a proportional valve.

27. The system of claim 23, wherein said sampling device comprises a thermal desorption unit.

28. The system of claim 23, wherein said sampling device comprises a headspace sampler.

29. A system for controlling the flow into a chromatographic column, comprising:
- a sampling device that obtains a sample gas containing analytes to be measured;
- a transfer line that communicates the sample gas from the sampling device to a chromatographic column, said transfer line having an inlet end and an outlet end;
- a valve that controls the pressure at the inlet end of said transfer line;
- a first pressure transducer that measures the pressure at the inlet end of said transfer line;
- a second pressure transducer for determining the pressure at the outlet end of the transfer line; and
- a controller that receives signals from said first and second transducers and, in response thereto, adjusts said valve to establish a desired flow rate at the outlet end of said transfer line;
- wherein said second pressure transducer is a differential pressure transducer that measures the pressure drop across the transfer line, and wherein said controller calculates the pressure at the outlet end of said transfer line from the measured pressure at the inlet end and the measured pressure drop.

* * * * *